(12) United States Patent
Shishimi et al.

(10) Patent No.: US 12,024,487 B2
(45) Date of Patent: Jul. 2, 2024

(54) METHOD FOR PRODUCING M-DIALKYLBENZALDEHYDE

(71) Applicant: MITSUBISHI GAS CHEMICAL COMPANY, INC., Chiyoda-ku (JP)

(72) Inventors: Toru Shishimi, Okayama (JP); Tatsuya Utamura, Okayama (JP); Yutaka Matsuura, Niigata (JP); Tatsuyuki Kumano, Okayama (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 297 days.

(21) Appl. No.: 17/634,097

(22) PCT Filed: Jul. 27, 2020

(86) PCT No.: PCT/JP2020/028667
§ 371 (c)(1),
(2) Date: Feb. 9, 2022

(87) PCT Pub. No.: WO2021/039230
PCT Pub. Date: Mar. 4, 2021

(65) Prior Publication Data
US 2022/0363622 A1 Nov. 17, 2022

(30) Foreign Application Priority Data
Aug. 23, 2019 (JP) .................................. 2019-153127

(51) Int. Cl.
*C07C 45/49* (2006.01)
*C07C 45/50* (2006.01)

(52) U.S. Cl.
CPC .................................. *C07C 45/50* (2013.01)

(58) Field of Classification Search
CPC ...................................................... C07C 45/49
See application file for complete search history.

(56) References Cited

U.S. PATENT DOCUMENTS

| 3,962,343 A | 6/1976 | Fujiyama et al. |
| 4,460,794 A | 7/1984 | Fujiyama et al. |
| 6,303,827 B1 | 10/2001 | Saleh et al. |
| 2005/0085670 A1 | 4/2005 | Kato et al. |
| 2009/0118547 A1 | 5/2009 | Kitamura et al. |
| 2015/0368175 A1 | 12/2015 | Wu |
| 2018/0282662 A1 | 10/2018 | Chi-Lam et al. |

FOREIGN PATENT DOCUMENTS

| CN | 1323287 A | 11/2001 |
| CN | 1660747 A | 8/2005 |
| CN | 101437784 A | 5/2009 |
| CN | 105143166 A | 12/2015 |

(Continued)

OTHER PUBLICATIONS

International Search Report dated Oct. 6, 2020 in PCT/JP2020/028667filed on Jul. 27, 2020, citing references AA-AC and AO-AQ therein, 2 pages.
Gattermann, L., et al., "Eine Synthese aromatischer Aldehyde", Berichte der deutschen chemischen Gesellschaft, Retrieved from the Internet: URL: https://doi.org/10.1002/cber.18970300288, [retrieved on Aug. 9, 2022], Jan. 1 1897 (Jan. 1, 1897), pp. 1622-1624, XP055949966.

(Continued)

*Primary Examiner* — Sikarl A Witherspoon
(74) *Attorney, Agent, or Firm* — Oblon, McClelland, Maier & Neustadt, L.L.P.

(57) ABSTRACT

An object of the present invention is to provide a method for producing m-dialkylbenzaldehyde by using a reaction starting material containing 1,4-dialkylbenzene. The method for producing m-dialkylbenzaldehyde represented by formula (3), comprising a step of allowing carbon monoxide to react on a reaction starting material containing 1,4-dialkylbenzene represented by formula (1) in the presence of a Bronsted acid and a Lewis acid, wherein the reaction starting material is 1,4-dialkylbenzene represented by formula (1), or a mixture of 1,4-dialkylbenzene represented by formula (1) and 1,3-dialkylbenzene represented by formula (2), containing 10 mol % or more of the 1,4-dialkylbenzene represented by formula (1), wherein in formulae (1) to (3), $R^1$ represents a methyl group or an ethyl group, and $R^2$ represents a chain or cyclic alkyl group having 3 or more and 6 or less carbon atoms that has a tertiary carbon at the benzyl position.

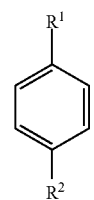

(1)

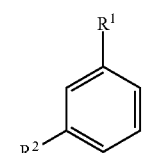

(2)

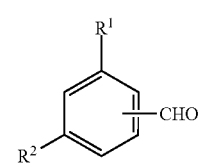

(3)

20 Claims, No Drawings

(56) References Cited

FOREIGN PATENT DOCUMENTS

JP          50-5344         1/1975
JP          56-99433 A      8/1981
JP       2017-533926 A     11/2017

OTHER PUBLICATIONS

Niedzielski, E. L., et al., "On the Mechanism of the Gattermann Reaction II", Journal of Organic Chemistry. Retrieved from the Internet: URL: https://pubs.acs.org/doi/pdf/10.1021/jo01190a004 [retrieved on Aug. 8, 2022], Jan. 1, 1943 (Jan. 1, 1943), pp. 147-152, XP055949640.

Chung et al., "Friedel-Crafts Acylation of ρ-Xylene over Sulfonated Zirconium, Teraphthalates", Catal Lett 144, 817-824 (2014), Published: Mar. 22, 2014, URL: https://doi.org/10.1007/s10562-014-1242-4.

Chiche et al., "Friedel-Crafts Acylation of Toluene and ρ-Xylene with Carboxylic Acids Catalyzed by Zeolites", J. Org. Chem. 51, 11, 2128-2130, (1986). Publication Date: May 1, 1986, URL: https://doi.org/10.1021/jo00361a039.

Graham, Heather, "Friedel-Crafts Acylation", Apr. 30, 2019, DOI:10.13140/RG.2.2.26865.12646.

METHOD FOR PRODUCING M-DIALKYLBENZALDEHYDE

CROSS-REFERENCE TO RELATED APPLICATIONS

The present application is a 35 U.S.C. § 371 national stage application of International patent application PCT/JP2020/028667, filed Jul. 27, 2020, which is based on and claims the benefit of priority to Japanese Application No. 2019-153127, filed Aug. 23, 2019. The entire contents of these applications are incorporated herein by reference.

TECHNICAL FIELD

The present invention relates to a method for producing m-dialkylbenzaldehyde.

BACKGROUND ART

Conventionally, alkylbenzaldehydes have been attracting attention for their use as fragrances and as starting materials for fragrances, and in these applications, not only aroma but also skin sensitization and biodegradability are of importance, and the substitution position of the substituent and the abundance ratio of the isomers are important for these properties.

Patent Literature 1 describes that carbon monoxide is allowed to react with 1-isobutyl-3-methylbenzene under pressure to directly introduce a formyl group at position 4.

CITATION LIST

Patent Literature

PTL1: JP 2017-533926A

SUMMARY OF INVENTION

Technical Problem

In the method described in Patent Literature 1, m-dialkylbenzaldehyde could not be obtained unless 1,3-dialkylbenzene was used as a starting material.

An object of the present invention is to provide a method for producing m-dialkylbenzaldehyde by using a reaction starting material containing 1,4-dialkylbenzene.

Solution to Problem

The present inventors have found, as a result of diligent investigation that m-dialkylbenzaldehyde can be produced by allowing carbon monoxide to react on a reaction starting material containing 1,4-dialkylbenzene in the presence of a Bronsted acid and a Lewis acid, and thus have completed the present invention.

Namely, the present invention is as follows.

<1> A method for producing m-dialkylbenzaldehyde represented by formula (3), comprising a step of allowing carbon monoxide to react on a reaction starting material containing 1,4-dialkylbenzene represented by formula (1) in the presence of a Bronsted acid and a Lewis acid, wherein the reaction starting material is 1,4-dialkylbenzene represented by formula (1), or a mixture of 1,4-dialkylbenzene represented by formula (1) and 1,3-dialkylbenzene represented by formula (2), containing 10 mol % or more of the 1,4-dialkylbenzene represented by formula (1).

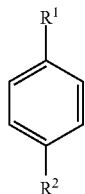

(1)

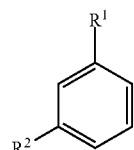

(2)

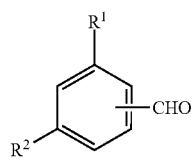

(3)

wherein in formulae (1) to (3), $R^1$ represents a methyl group or an ethyl group, and $R^2$ represents a chain or cyclic alkyl group having 3 or more and 6 or less carbon atoms that has a tertiary carbon at the benzyl position.

<2> The method according to <1>, wherein a Bronsted acid and a Lewis acid (Bronsted acid/Lewis acid) are $HF/BF_3$ or $HCl/AlCl_3$.

<3> The method according to <1> or <2>, wherein a compound represented by formula (1) is selected from the group consisting of the following formulae (1-1) to (1-7).

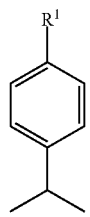

(1-1)

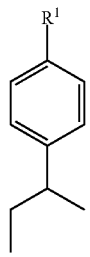

(1-2)

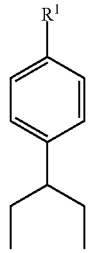

(1-3)

(1-4)

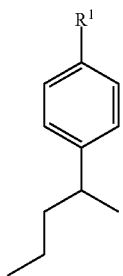

(1-5)

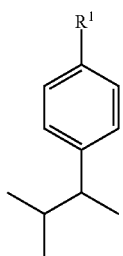

(1-6)

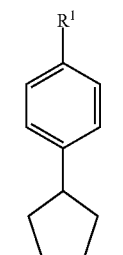

(1-7)

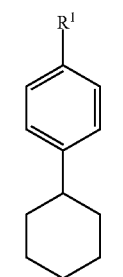

wherein in the formula, $R^1$ represents a methyl group or an ethyl group.

<4> The method according to any one of <1> to <3>, wherein a temperature at which carbon monoxide reacts is −30° C. or higher and 30° C. or lower.

<5> The method according to any one of <1> to <4>, wherein a Bronsted acid and a Lewis acid (Bronsted acid/Lewis acid) are $HF/BF_3$, and a molar ratio of HF and a reaction starting material (the HF/the reaction starting material) is 5.0 or more and 25.0 or less.

<6> The method according to any one of <1> to <5>, wherein a Bronsted acid and a Lewis acid (Bronsted acid/Lewis acid) are $HF/BF_3$, and a molar ratio of $BF_3$ and a reaction starting material (the $BF_3$/the reaction starting material) is 0.2 or more and 2.5 or less.

<7> The method according to any one of <1> to <4>, wherein a Bronsted acid and a Lewis acid (Bronsted acid/Lewis acid) are $HCl/AlCl_3$, and a molar ratio of HCl and a reaction starting material (the HCl/the reaction starting material) is 0.0001 or more and 0.3 or less.

<8> The method according to any one of <1> to <4> and <7>, wherein a Bronsted acid and a Lewis acid (Bronsted acid/Lewis acid) are $HCl/AlCl_3$, and a molar ratio of $AlCl_3$ and a reaction starting material (the $AlCl_3$/the reaction starting material) is 0.2 or more and 2.5 or less.

<9> The method according to any one of <1> to <8>, wherein a reaction pressure is 1.0 MPaG or more and 3.0 MPaG or less.

<10> The method according to any one of <1> to <9>, wherein the reaction starting material is a mixture of 1,4-dialkylbenzene represented by formula (1) and 1,3-dialkylbenzene represented by formula (2), containing 10 mol % or more of 1,4-dialkylbenzene represented by formula (1).

Advantageous Effects of Invention

According to the present invention, it is possible to provide a method for producing m-dialkylbenzaldehyde by using a reaction starting material containing 1,4-dialkylbenzene.

DESCRIPTION OF EMBODIMENTS

[Method for Producing m-Dialkylbenzaldehyde]

The method for producing m-dialkylbenzaldehyde represented by formula (3) of the present invention (hereinafter, also simply referred to as "the production method of the present invention") is a production method comprising a step of allowing carbon monoxide to react on a reaction starting material containing 1,4-dialkylbenzene represented by formula (1) in the presence of a Bronsted acid and a Lewis acid, and the reaction starting material is 1,4-dialkylbenzene represented by formula (1), or a mixture of 1,4-dialkylbenzene represented by formula (1) and 1,3-dialkylbenzene represented by formula (2), containing 10 mol % or more of the 1,4-dialkylbenzene represented by formula (1).

(1)

(2)

(3)

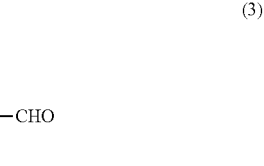

wherein in formulae (1) to (3), $R^1$ represents a methyl group or an ethyl group, and $R^2$ represents a chain or cyclic alkyl group having 3 or more and 6 or less carbon atoms that has a tertiary carbon at the benzyl position.

According to the present invention, 1,4-dialkylbenzene represented by formula (1) (hereinafter, also simply referred to as "1,4-dialkylbenzene" or "p-dialkylbenzene"), or a mixture of 1,4-dialkylbenzene represented by formula (1)

and 1,3-dialkylbenzene represented by formula (2) (hereinafter, also simply referred to as "1,3-dialkylbenzene" or "m-dialkylbenzene"), containing 10 mol % or more of 1,4-dialkylbenzene represented by formula (1), is used as a starting material, and m-dialkylbenzaldehyde represented by formula (3) (hereinafter, also simply referred to as "m-dialkylbenzaldehyde") is obtained.

The production method of the present invention when the reaction starting material is p-dialkylbenzene is as shown in the following formula (I), and the production method of the present invention when the reaction starting material is a mixture of p-dialkylbenzene and m-dialkylbenzene is as the following formula (II).

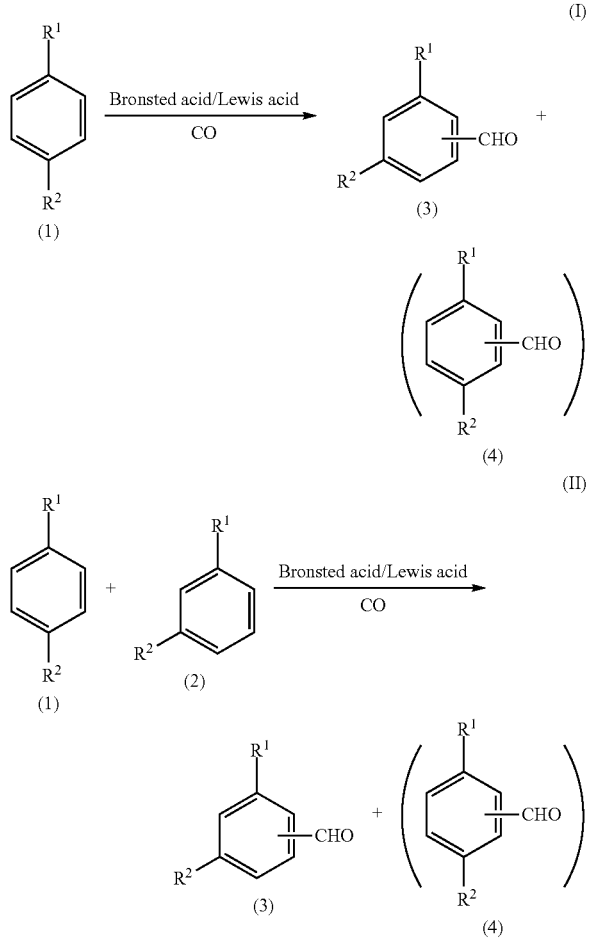

In reaction formulae (I) and (II), $R^1$ and $R^2$ are as described above.

By reacting p-dialkylbenzene, or the mixture of p-dialkylbenzene and m-dialkylbenzene with carbon monoxide in the presence of a Bronsted acid and a Lewis acid, m-dialkylbenzaldehyde (the compound represented by formula (3)) is obtained, however, p-dialkylbenzaldehyde represented by formula (4) is produced as a by-product.

Moreover, the compound represented by formula (3) is a mixture of 2-$R^1$-4-$R^2$ benzaldehyde represented by the following formula (3-1) and 4-$R^1$-2-$R^2$-benzaldehyde represented by formula (3-2), however, the compound represented by formula (3-1) is a main product, and the compound represented by formula (3-2) is a by-product.

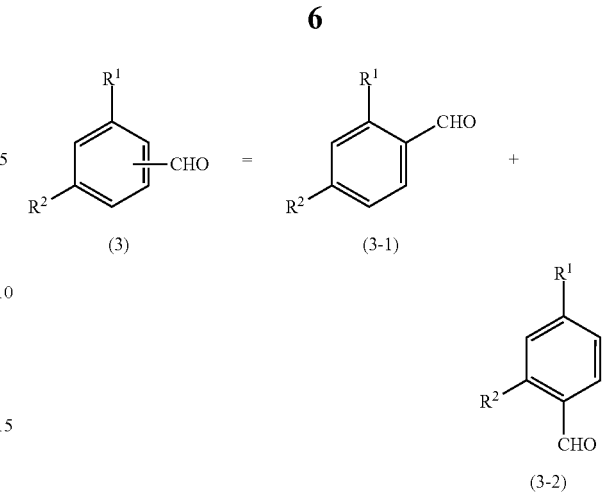

Conventionally, as described in Patent Literature 1, m-dialkylbenzaldehyde has been obtained by using m-dialkylbenzene as a starting material, but some m-dialkylbenzenes are produced in small amounts and are expensive, and therefore a method for producing m-dialkylbenzaldehyde having excellent regioselectivity, which can be derived from an inexpensive material, has been demanded.

The present inventors have found that m-dialkylbenzaldehyde in which the alkyl group was rearranged and isomerized can be obtained by allowing carbon monoxide to react on a starting material containing p-dialkylbenzene with a specific structure in the presence of a Bronsted acid and a Lewis acid.

The detailed reason why the above reaction occurs is unknown, but it is conjectured that use of p-dialkylbenzene as a starting material, in which $R^2$ in formula (1) is a chain or cyclic alkyl group having 3 or more and 6 or less carbon atoms that has a tertiary carbon at the benzyl position, stabilizes the positive charge on the carbon at the benzyl position, isomerizes to more thermodynamically stable m-dialkylbenzene, and subsequently allows proceeding with formylation.

The substitution position of the formyl group in the m-dialkylbenzaldehyde obtained is not particularly limited, but the yield of 2,4-dialkylbenzaldehyde tends to be high due to steric hindrance and electron density, and as described above, the yield of 2,4-dialkylbenzaldehyde in which position 2 is $R^1$ and position 4 is $R^2$, tends to be higher.

Hereinafter, the present invention will be described in detail.

<Reaction Starting Material>

In the present invention, p-dialkylbenzene (the compound represented by formula (1)) or a mixture of p-dialkylbenzene and m-dialkylbenzene (the compound represented by formula (2)), containing 10 mol % or more of p-dialkylbenzene (hereinafter, also simply referred to as "mixture") is used as a reaction starting material.

[Compound Represented by Formula (1)]

In the above formula (1), $R^1$ represents a methyl group or an ethyl group, and $R^2$ represents a chain or cyclic alkyl group having 3 or more and 6 or less carbon atoms that has a tertiary carbon at the benzyl position.

$R^1$ is preferably a methyl group from the viewpoint of reactivity.

When $R^2$ is a chain alkyl group, $R^2$ preferably has 3 or more and 5 or less carbon atoms. Examples of $R^2$ include an isopropyl group, a 1-methylpropyl group, a 1-ethylpropyl group, a 1-methylbutyl group and a 1,2-dimethylpropyl group.

When $R^2$ is a cyclic alkyl group, $R^2$ preferably has 4 or more and 6 or less carbon atoms and more preferably 5 or more and 6 or less carbon atoms.

The compound represented by formula (1) is preferably selected from the group consisting of the following formulae (1-1) to (1-7).

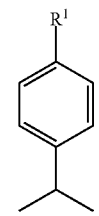

(1-1)

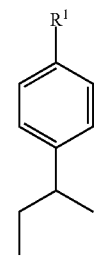

(1-2)

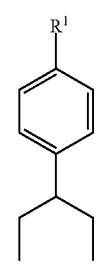

(1-3)

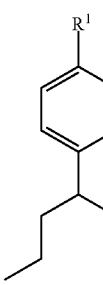

(1-4)

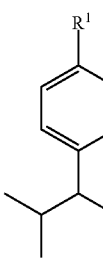

(1-5)

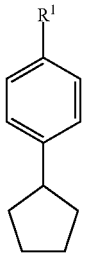

(1-6)

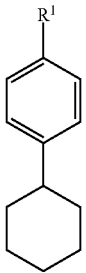

(1-7)

wherein in the formula, $R^1$ represent a methyl group or an ethyl group.

Among them, the compounds represented by formulae (1-1), (1-2), (1-6), and (1-7) are preferable, the compounds represented by formulae (1-1) and (1-7) are more preferable, and the compound represented by formula (1-1) is still more preferable from the viewpoints of reactivity, yield, and selectivity of the compound obtained.

[Mixture]

When a mixture of p-dialkylbenzene and m-dialkylbenzene is used as the starting material, the content of p-dialkylbenzene is 10 mol % or more.

The production method of the present invention is characterized in that it uses a reaction starting material containing p-dialkylbenzene.

The content of p-dialkylbenzene in the mixture is preferably 15 mol % or more, more preferably 20 mol % or more, still more preferably 25 mol % or more, and even still more preferably 30 mol % or more. Even if the content of p-dialkylbenzene in the mixture is high, m-dialkylbenzaldehyde can be efficiently obtained.

The upper limit of the content of p-dialkylbenzene in the mixture is not particularly limited and is less than 100 mol %.

For example, isopropyltoluene as a mixture of m-isopropyltoluene and p-isopropyltoluene can be obtained at a lower cost than single m-isopropyltoluene, and in the present invention, the target m-dialkylbenzaldehyde can be produced by reacting with the mixture as it is as well by using such an inexpensively available starting material.

In the present invention, the reaction starting material is preferably a mixture of p-dialkylbenzene and m-dialkylbenzene, containing 10 mol % or more of p-dialkylbenzene from the viewpoint of availability and economic efficiency.

<Bronsted Acid and Lewis Acid>

In the production method of the present invention, carbon monoxide is allowed to react with a reaction starting material containing p-dialkylbenzene in the presence of a Bronsted acid and a Lewis acid.

The present invention utilizes the Gattermann-Koch reaction, which is a method for synthesizing an aromatic aldehyde from alkylbenzene and carbon monoxide in the presence of a Bronsted acid and a Lewis acid, and in the past, a combination of HCl/AlCl$_3$ was used in which HCl was used as the Bronsted acid and AlCl$_3$ was used as the Lewis acid. The combination of Bronsted acid and Lewis acid is not limited thereto, and may be, for example, HF/SbF$_5$, CF$_3$SO$_3$H/SbF$_5$, and HF/BF$_3$.

Among them, HF/BF$_3$ or HCl/AlCl$_3$ is preferred as the combination of Bronsted acid and Lewis acid (Bronsted acid/Lewis acid), and HF/BF$_3$ is more preferred from the viewpoint of reactivity, yield, and selectivity.

HF used as a Bronsted acid also has a function as a solvent for the reaction. The HF is preferably a substantially anhydrous HF from the viewpoint of reactivity. The substantially anhydrous refers to having a content of water being substantially 5% by mass or less, preferably 1% by mass or less, and more preferably 0.1% by mass or less.

When HF/BF$_3$ is used as a combination of Bronsted acid and Lewis acid (Bronsted acid/Lewis acid), the molar ratio of HF that is a Bronsted acid, and the reaction starting material (the HF/the reaction starting material) is preferably 5.0 or more, more preferably 6.0 or more, and still more preferably 7.0 or more from the viewpoint of reactivity with carbon monoxide and inhibiting the side reactions, and it is preferably 25.0 or less, more preferably 22.0 or less, and still more preferably 18.0 or less from the viewpoints of economic efficiency and production efficiency.

Moreover, when HF/BF$_3$ is used as a combination of Bronsted acid and Lewis acid (Bronsted acid/Lewis acid), the molar ratio of BF$_3$ that is a Lewis acid, and a reaction starting material (the BF$_3$/the reaction starting material) is preferably 0.2 or more, more preferably 0.5 or more and still more preferably 1.0 or more from the viewpoints of improving the conversion ratio and improving the production efficiency, and it is preferably 2.5 or less, more preferably 2.2 or less, and still more preferably 1.8 or less from the viewpoint of economic efficiency.

When HCl/AlCl$_3$ is used as a combination of Bronsted acid and Lewis acid (Bronsted acid/Lewis acid), the molar ratio of HCl that is a Bronsted acid, and a reaction starting material (the HCl/the reaction starting material) is preferably 0.0001 or more, more preferably 0.001 or more, and still more preferably 0.01 or more, and preferably 0.3 or less, more preferably 0.1 or less, and still more preferably 0.05 or less, from the viewpoint of reactivity with carbon monoxide and inhibiting the side reactions.

When HCT/AlCl$_3$ is used as a combination of Bronsted acid and Lewis acid (Bronsted acid/Lewis acid), the molar ratio of AlCl$_3$ that is a Lewis acid, and a reaction starting material (the AlCl$_3$/the reaction starting material) is preferably 0.2 or more, more preferably 0.5 or more, and still more preferably 1.0 or more from the viewpoints of improving the conversion ratio and improving the production efficiency, and it is preferably 2.5 or less, more preferably 2.2 or less, and still more preferably 1.8 or less from the viewpoint of economic efficiency.

<Reaction Temperature>

In the present invention, carbon monoxide is allowed to react with the reaction starting material containing m-dialkylbenzene in the presence of the Bronsted acid and the Lewis acid.

The temperature at which carbon monoxide reacts upon the reaction is preferably −30° C. or higher and more preferably −27° C. or higher, and preferably 30° C. or lower, more preferably 15° C. or lower, and still more preferably 5° C. or lower from the viewpoints of improving reactivity, inhibiting the side reactions, and improving regioselectivity in which a formyl group is introduced.

When HF/BF$_3$ is used as a combination of Bronsted acid and Lewis acid (Bronsted acid/Lewis acid), the reaction temperature is preferably −30° C. or higher and more preferably −27° C. or higher, and preferably 10° C. or lower, more preferably −5° C. or lower, and still more preferably −15° C. or lower, from the viewpoints of improving the reactivity and inhibiting side reactions.

Moreover, when HCl/AlCl$_3$ is used as a combination of Bronsted acid and Lewis acid (Bronsted acid/Lewis acid), the reaction temperature is preferably −15° C. or higher, more preferably −10° C. or higher, and still more preferably −5° C. or higher, and preferably 30° C. or lower, more preferably 15° C. or lower, and still more preferably 5° C. or lower, from the viewpoints of improving reactivity and inhibiting the side reactions.

The reaction between the reaction starting material and carbon monoxide is preferably carried out under pressure.

The pressure upon reaction is preferably 1.0 MPaG or more, more preferably 1.5 MPaG or more, and still more preferably 1.8 MPaG or more, and preferably 3.0 MPaG or less, more preferably 2.5 MPaG or less, and still more preferably 2.2 MPaG or less, from the viewpoints of improving reactivity and inhibiting the side reactions.

In the present invention, the reaction time is not particularly limited, but is preferably 10 minutes or longer, more preferably 20 minutes or longer, and still more preferably 30 minutes or longer, and preferably 5 hours or shorter, more preferably 3 hours or shorter, and still more preferably 1.5 hours or shorter, from the viewpoints of sufficiently allowing the reaction to proceed, and inhibiting the side reactions and decomposition of products as well as efficiently producing the product.

Further, the production method of the present invention may be carried out in the presence of a solvent. The solvent used is not particularly limited as long as it dissolves well the reaction starting material and is inactive to the Bronsted acid and Lewis acid used. Examples thereof include saturated aliphatic hydrocarbons such as hexane, heptane and decane, aromatic hydrocarbons such as benzene and toluene, and halogenated aliphatic hydrocarbons such as chloroform, methylene chloride and dichloroethane. These solvents may be used alone or in combination of two or more.

The amount of the solvent used is not particularly limited and may be appropriately selected from the viewpoints of reaction uniformity, reaction rates, and removal of the solvent.

When HF is used as the Bronsted acid, for example, HF also functions as a solvent, and therefore a solvent may not be used, and preferably a solvent is not used because there is no need to remove the solvent.

The mode of the production method of the present invention is not particularly limited, and any method such as a batch type, semi-batch type, continuous type, etc., may be employed. When the Bronsted acid/Lewis acid is HF/BF$_3$, the continuous type is preferred due to the ability to recover and reuse the catalyst and from the viewpoint of production efficiency, and when it is HCl/AlCl$_3$, the batch type is preferred from the viewpoint of being suitable for charging solid AlCl$_3$.

Further, the apparatus used in the production method is a reaction apparatus that can sufficiently mix a liquid phase and a gas phase while adjusting a temperature under pressure.

For example, in the batch type, a reaction starting material, a Bronsted acid, a Lewis acid, and a solvent if necessary, are charged in a reactor with a stirrer, the contents are stirred, the liquid temperature is preferably maintained at −30° C. or higher and 30° C. or lower, then the pressure is preferably increased to 1.0 to 3.0 MPaG by carbon monoxide, subsequently the pressure and liquid temperature are maintained as they are and held for 10 minutes to 5 hours until carbon monoxide is no longer absorbed, and then the reaction product solution is discharged to obtain m-dialkylbenzaldehyde.

Moreover, in the semi-batch type, a Bronsted acid and a Lewis acid are charged in a reactor with a stirrer, the contents are stirred, the liquid temperature is preferably set to −30° C. or higher and 30° C. or lower, the temperature is allowed to be in a constant state, subsequently the pressure is preferably increased to 1.0 to 3.0 MPaG by carbon monoxide so that carbon monoxide can be supplied so as to keep the pressure constant. Then, a reaction starting material dissolved in a solvent if necessary is supplied, and after the supply is completed, the reactant is held for 10 minutes to 5 hours until the absorption of carbon monoxide is completed followed by discharge of the reaction product liquid to obtain m-dialkylbenzaldehyde.

Further, in the continuous type, first, a Bronsted acid and a Lewis acid are charged into a reactor with a stirrer, the contents are stirred, the liquid temperature is preferably set to −30° C. or higher and 30° C. or lower, the temperature is allowed to be in a constant state, subsequently the pressure is preferably increased to 1.0 to 3.0 MPaG by carbon monoxide so that carbon monoxide can be supplied so as to keep the pressure constant. Then, a semi-batch reaction is carried out in which a reaction starting material dissolved in a solvent if necessary is supplied. Further, the Bronsted acid, the Lewis acid, and the reaction starting material dissolved in the solvent, if necessary, are started to be supplied, and the reaction product liquid is continuously discharged. The time for the reaction liquid to stay in the reactor is preferably 10 minutes to 5 hours. By setting the residence time to 10 minutes to 5 hours, m-dialkylbenzaldehyde can be efficiently produced.

After removing the Bronsted acid and Lewis acid from the obtained reaction liquid containing m-dialkylbenzaldehyde, it can be purified by a conventional method such as distillation or extraction.

EXAMPLES

Hereinafter, the present invention will be described in more detail with reference to Examples, but the present invention is not limited to these Examples.

The reaction results were evaluated by the following formulae.

Conversion ratio (mol %)={1−(Amount of substance (number of moles) of reaction starting material remaining after reaction)/(Amount of substance (number of moles) charged of reaction starting material)}×100

Selectivity (mol %)=Amount of substance (number of moles) of target compound/Amount of substance (number of moles) of reaction starting material consumed by reaction×100

Yield (mol %)=Conversion ratio×selectivity/100

It is noted that the amount of each substance (number of moles) was calculated by dividing the peak area by GC analysis by the molecular weight and taking the ratio thereof.

<Gas Chromatography Analysis (GC Analysis)>
Equipment: GC-2010 Plus (manufactured by Shimadzu Corporation)
Detector: FID
Column: DB-1 (Capillary Column manufactured by Agilent Technologies)
(0.32 mmφ×30 m×0.50 μm)
Temperature rise conditions: The temperature is raised at a rate of temperature rise of 5° C./min from 100° C. to 310° C. and the temperature is held at 310° C. for 20 minutes.
<NMR Spectrum Analysis>
Apparatus 1: Bruker Avance 2 600 MHz-NMR
(5 mm Cryo-CPDUL Probe) (manufactured by Bruker Corporation)
Apparatus 2: Bruker Avance 3 HD 500 MHz-NMR
(5 mm BBO CryoProbe) (manufactured by Bruker Corporation)
Solvent: Deuterated chloroform ($CDCl_3$)
Measurement mode: $^1H$, $^{13}C$, HSQC, Dept (90 deg), HMBC
Internal standard substance: Tetramethylsilane (TMS)
It is noted that apparatus 1 was used for the measurement of $^1H$, $^{13}C$ and Dept (90 deg), and apparatus 2 was used for the measurement of HSQC and HMBC.

Example 1

A 500 mL autoclave equipped with a NAC drive type stirrer, three inlet nozzles at the top and one outlet nozzle at the bottom, an internal temperature of which can be controlled by a jacket, was used as a formylation reactor.

A refrigerant was poured through the jacket, and 126.5 g (6.32 mol) of hydrogen fluoride was charged into the autoclave cooled to −25° C.

After that, 42.6 g (0.63 mol) of boron trifluoride was added with stirring while adjusting the temperature not to exceed −25° C.

Following addition of boron trifluoride, the temperature inside the autoclave was maintained at −25° C. and the pressure was increased to 2 MPaG with carbon monoxide, and 56.7 g (0.42 mol) of m, p-mixed cymene (isopropyl-toluene, m:p (molar ratio))=68.3:31.7) was added.

After stirring for 45 minutes while maintaining a temperature of −25° C. and a pressure of 2 MPaG, the liquid reaction mixture in the autoclave was drained into ice water. The drained liquid was shaken well, and then the oil layer was separated. After washing the obtained oil layer with water, it was analyzed by gas chromatography (GC), resulting that the conversion ratio of m, p-mixed cymene was 98.9 mol %, the selectivity of 4-isopropyl-2-methylbenzaldehyde was 85.9 mol %, the selectivity of 2-isopropyl-4-methylbenzaldehyde was 11.0 mol %, and the selectivity of the two isomers in total was 96.9 mol %.

Examples 2 to 5 m-Dialkylbenzaldehyde was produced in the same manner as in Example 1 except that the reaction conditions and the type of the reaction starting material used were changed as shown in Table 1.

The results are shown in Table 1.

The GC peak was assigned by purifying the sample subjected to GC-analysis in Example 3 by flash distillation and structurally analyzing the fraction by NMR.

By the NMR analysis, the main products were identified to be 4-isopropyl2-methyl-benzaldehyde and 2-isopropyl-4-methylbenzaldehyde. The result of $^1H$-NMR peak area and the result of GC analysis were in favorable agreement with each other.

The results of NMR spectrum analysis are shown below.

4-Isopropyl 2-methyl-benzaldehyde $^1$H NMR (600 MHz, CDCl$_3$) δ 1.26-1.27 (6H, d, J=6.6 Hz, [9]), 2.65 (3H, s, [10]), 2.89-2.96 (1H, sep, J=6.6 Hz, [8]), 7.11 (1H, s, [6]), 7.21-7.22 (1H, d, J=7.8 Hz, [7]), 7.72-7.73 (1H, d, J=7.8 Hz, [4]), 10.2 (1H, s, [1])

$^{13}$C NMR (150 MHz, CDCl$_3$) δ 19.8 [10], 23.6 [9], 34.3 [8], 124.4 [7], 130.0 [6], 132.3 [5], 132.6 [4], 140.8 [3], 155.3 [2], 192.4 [1]

$^{13}$C NMR (150 MHz, CDCl$_3$) δ 22.0 [10], 23.8 [9], 27.5 [8], 126.8 [7], 126.9 [6], 130.7 [5], 132.0 [4], 144.9 [3], 151.5 [2], 192.0 [1]

*1: The signal is difficult to read appropriately because of overlapping with the peak of 4-isopropyl-2-methyl-benzaldehyde.

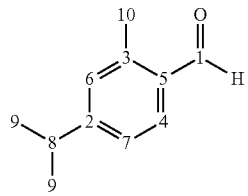

[Chemical Formula 10]

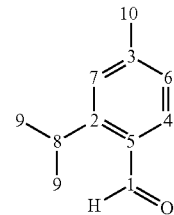

[Chemical Formula 11]

TABLE 1

|  |  | Example 1 | Example 2 | Example 3 | Example 4 | Example 5 |
|---|---|---|---|---|---|---|
| Reaction starting material | R$^1$ | Methyl | Methyl | Methyl | Methyl | Methyl |
|  | R$^2$ | Isopropyl | Isopropyl | Isopropyl | Isopropyl | Cyclohexyl |
|  | m-isomer:p-isomer [mol:mol] | 68.3:31.7 | 0:100 | 68.3:31.7 | 0:100 | 0:100 |
| Charging | Reaction starting material(g) | 56.7 g | 55.7 g | 87.4 g | 89.1 g | 83.0 g |
|  | [mol] | (0.42 mol) | (0.41 mol) | (0.65 mol) | (0.66 mol) | (0.48 mol) |
|  | HF(g) | 126.5 g | 124.1 g | 97.6 g | 99.5 g | 95.3 g |
|  | [mol] | (6.32 mol) | (6.20 mol) | (4.88 mol) | (4.97 mol) | (4.76 mol) |
|  | BF$_3$(g) | 42.6 g | 42.1 g | 66.2 g | 67.6 g | 48.5 g |
|  | [mol] | (0.63 mol) | (0.62 mol) | (0.98 mol) | (1.00 mol) | (0.72 mol) |
|  | CO [MPaG] | Filled up to 2.0 MPaG | Filled up to 2.0 MPaG | Filled up to 2.0 MPaG | Filled up to 2.0 MPaG | Filled up to 2.0 MPaG |
| Reaction conditions | Reaction temperature [° C.] | −25 | −25 | −25 | −25 | −25 |
|  | Reaction time [min.] | 45 | 45 | 45 | 45 | 45 |
|  | Pressure [MPaG] | 2.0 | 2.0 | 2.0 | 2.0 | 2.0 |
|  | HF/reaction starting material [mol/mol] | 15.0 | 15.1 | 7.5 | 7.5 | 9.9 |
|  | BF$_3$/reaction starting material [mol/mol] | 1.5 | 1.5 | 1.5 | 1.5 | 1.5 |
| Reaction results | Conversion ratio [%] | 98.9 | 98.4 | 99.2 | 99.3 | 99.5 |
| 4-alkyl*-2-methylbenzaldehyde | Selectivity [%] | 85.9 | 78.0 | 78.8 | 69.7 | 65.1 |
|  | Yield [%] | 85.0 | 76.8 | 78.2 | 69.2 | 64.8 |
| 2-alkyl*-4-methylbenzaldehyde | Selectivity [%] | 11.0 | 10.5 | 9.5 | 8.6 | 10.1 |
|  | Yield [%] | 10.9 | 10.3 | 9.4 | 8.5 | 10.0 |
| Total of isomers | Selectivity [%] | 96.9 | 88.5 | 88.3 | 78.3 | 75.2 |
|  | Yield [%] | 95.8 | 87.1 | 87.6 | 77.8 | 74.8 |

*Examples 1 to 4: Alkyl = isopropyl, Example 5: Alkyl = cyclohexyl

2-Isopropyl-4-methyl-benzaldehyde $^1$H NMR (600 MHz, CDCl$_3$) δ 1.28-1.30 (6H, d, J=7.2 Hz, [9]), 2.41 (3H, s, [10]), 3.93-4.00 (1H, sep, J=7.2 Hz, [8]), 7.14-7.15 (1H, d, J=7.8 Hz, [6]), 7.24 (1H, s, [7]), 7.70-7.72 (1H, m*$^1$, [4]), 10.29 (1H, s, [1])

Comparative Examples 1 to 3

Dialkylbenzaldehyde was produced in the same manner as in Example 1 except that the reaction conditions and the type of p-dialkylbenzene used were changed as shown in Table 2.

The results are shown in Table 2.

TABLE 2

|  |  | Comparative Example 1 | Comparative Example 2 | Comparative Example 3 |
|---|---|---|---|---|
| Reaction starting material | R$^1$ | Methyl | Methyl | Methyl |
|  | R$^2$ | Ethyl | Normal propyl | Isobutyl |
|  | m-isomer:p-isomer [mol:mol] | 0:100 | 0:100 | 0:100 |
| Charging | Reaction starting material (g) [mol] | 42.6 g (0.35 mol) | 46.1 g (0.34 mol) | 43.1 g (0.29 mol) |

TABLE 2-continued

|  |  | Comparative Example 1 | Comparative Example 2 | Comparative Example 3 |
|---|---|---|---|---|
|  | HF(g) [mol] | 53.1 g (2.65 mol) | 51.6 g (2.58 mol) | 43.6 g (2.18 mol) |
|  | $BF_3$(g) [mol] | 35.9 g (0.53 mol) | 35.9 g (0.53 mol) | 29.4 g (0.43 mol) |
|  | CO [MPaG] | Filled up to 2.0 MPaG | Filled up to 2.0 MPaG | Filled up to 2.0 MPaG |
| Reaction conditions | Reaction temperature [° C.] | −25 | −25 | −25 |
|  | Reaction time [min.] | 45 | 45 | 45 |
|  | Pressure [MPaG] | 2.0 | 2.0 | 2.0 |
|  | HF/reaction starting material [mol/mol] | 7.6 | 7.6 | 7.5 |
|  | $BF_3$/reaction starting material [mol/mol] | 1.5 | 1.6 | 1.5 |
| Reaction results | Conversion ratio [%] | 95.8 | 96.6 | 93.8 |
| 4-alkyl*-2-methylbenzaldehyde | Selectivity [%] | 3.7 | 1.4 | 0.5 |
|  | Yield [%] | 3.5 | 1.4 | 0.5 |
| 2-alkyl*-4-methylbenzaldehyde | Selectivity [%] | 1.8 | 0.4 | 0.0 |
|  | Yield [%] | 1.7 | 0.4 | 0.0 |
| Total of isomers | Selectivity [%] | 5.5 | 1.8 | 0.5 |
|  | Yield [%] | 5.3 | 1.7 | 0.5 |
| Reaction results | Conversion ratio [%] | 95.8 | 96.6 | 93.8 |
| 5-alkyl*-2-methylbenzaldehyde | Selectivity [%] | 66.2 | 73.2 | 85.2 |
|  | Yield [%] | 63.4 | 70.7 | 79.9 |
| 2-alkyl*-5-methylbenzaldehyde | Selectivity [%] | 22.2 | 21.7 | 13.5 |
|  | Yield [%] | 21.3 | 21.0 | 12.7 |
| Total of isomers | Selectivity [%] | 88.4 | 94.9 | 98.7 |
|  | Yield [%] | 84.7 | 91.7 | 92.6 |

*Comparative Example 1: Alkyl = ethyl, Comparative Example 2: Alkyl = normal propyl, Comparative Example 3: Alkyl = isobutyl Example 6

A 500 mL autoclave equipped with a NAC drive type stirrer, three inlet nozzles at the top and one outlet nozzle at the bottom, an internal temperature of which can be controlled by a jacket, was used as a formylation reactor.

A refrigerant was poured through the jacket, and 74.5 g (0.56 mol) of aluminum chloride, 147.4 g (1.49 mol) of 1,2-dichloroethane (1,2-DCE), and 1 mL (0.01 mol) of 35% hydrochloric acid were charged in the autoclave cooled to 0° C.

Then, the temperature inside the autoclave was maintained at 0° C. under stirring, the pressure was increased to 2 MPaG with carbon monoxide, and 50.0 g (0.37 mol) of p-cymene was added.

After stirring for 60 minutes while maintaining the temperature at 0° C. and the pressure of 2 MPaG, the liquid reaction mixture in the autoclave was drained into ice water. The drained liquid was shaken well, and then the oil layer was separated. The obtained oil layer was washed with water and then analyzed by gas chromatography, resulting that the conversion ratio of m, p-mixed cymene was 79.7 mol %, the selectivity of 4-isopropyl-2-methylbenzaldehyde was 22.7 mol %, the selectivity of 2-isopropyl-4-methylbenzaldehyde was 4.5 mol %, and the selectivity of the two isomers in total was 27.2 mol %.

The results are shown in Table 3.

TABLE 3

|  |  | Example 6 |
|---|---|---|
| Reaction starting material Charging | $R^1$ | Methyl |
|  | $R^2$ | Isopropyl |
|  | m-isomer:p-isomer | 0:100 |
|  | Reaction starting material (g) [mol] | 50.0 g (0.37 mol) |

TABLE 3-continued

|  |  | Example 6 |
|---|---|---|
|  | 35% HCl (mL) [mol] | 1.0 mL (0.01 mol) |
|  | $AlCl_3$ (g) [mol] | 74.5 g (0.56 mol) |
|  | CO [MPaG] | Filled up to 2.0 MPaG |
|  | Solvent (1,2-DCE) (g) | 147.4 g |
| Reaction conditions | Reaction temperature [° C.] | 0 |
|  | Reaction time [min.] | 60 |
|  | Pressure [MPaG] | 2.0 |
|  | HCl/Reaction starting material [mol/mol] | 0.03 |
|  | $AlCl_3$/Reaction starting material [mol/mol] | 1.5 |
| Reaction results | Conversion ratio [%] | 79.7 |
| 4-isopropyl-2-methylbenzaldehyde | Selectivity [%] | 22.7 |
|  | Yield [%] | 18.1 |
| 2-isopropyl-4-methylbenzaldehyde | Selectivity [%] | 4.5 |
|  | Yield [%] | 3.6 |
| Total of isomers | Selectivity [%] | 27.2 |
|  | Yield [%] | 21.7 |

According to the results in Table 1, it was shown that m-dialkylbenzaldehyde could be efficiently produced from p-dialkylbenzene by the production method of the present invention. As shown in Table 2, it was shown that when p-dialkylbenzene not having a chain or cyclic alkyl group having 3 or more and 6 or less carbon atoms that has a tertiary carbon at the benzyl position was used as the reaction starting material, only an extremely small amount of the target m-dialkylbenzaldehyde was obtained because almost no isomerization occurred. Furthermore, it was shown from the results in Table 3 that m-dialkylbenzaldehyde could be produced from p-dialkylbenzene even when HCl and $AlCl_3$, were used as a Bronsted acid and a Lewis acid.

INDUSTRIAL APPLICABILITY

According to the present invention, it is possible to provide a method for producing m-dialkylbenzaldehyde by using the reaction starting material containing 1,4-dialkylbenzene, and the m-dialkylbenzaldehyde obtained is considered to be useful as a synthesis starting material compound such as a fragrance starting material.

The invention claimed is:

1. A method for producing m-dialkylbenzaldehyde of formula (3), comprising:
    contacting a reaction starting material with carbon monoxide in a presence of a Bronsted acid and a Lewis acid such that the carbon monoxide reacts on the reaction starting material which comprises either 1,4-dialkylbenzene of formula (1), or a mixture of 1,4-dialkylbenzene of the formula (1) and 1,3-dialkylbenzene of formula (2), the mixture comprising 10 mol % or more of the 1,4-dialkylbenzene,

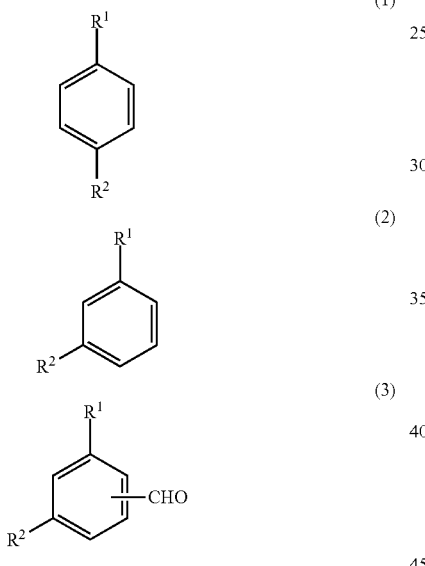

wherein $R^1$ is a methyl group or an ethyl group, and $R^2$ is a chain or cyclic alkyl group having 3 to 6 carbon atoms and has a tertiary carbon at the benzyl position.

2. The method according to claim 1, wherein the Bronsted acid is HF, and the Lewis acid is $BF_3$ or
the Bronsted acid is HCl, and the Lewis acid is $AlCl_3$.

3. The method according to claim 1, wherein the 1,4-dialkylbenzene of the formula (1) is selected from the group consisting of compounds of formulae (1-1) to (1-7),

(1-1)

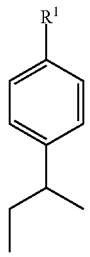

(1-2)

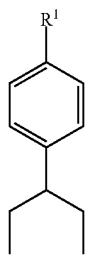

(1-3)

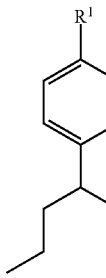

(1-4)

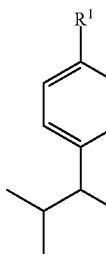

(1-5)

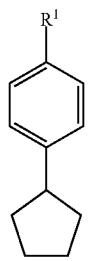

(1-6)

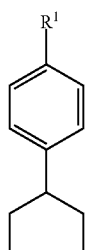

(1-7)

wherein $R^1$ is a methyl group or an ethyl group.

4. The method according to claim 1, wherein the reaction starting material is contacted with the carbon monoxide to react at a temperature in a range of from −30° C. to 30° C.

5. The method according to claim 1, wherein the Bronsted acid is BF and the Lewis acid is $BF_3$, and
wherein a molar ratio of HF to the reaction starting material is from 5.0 to 25.0.

6. The method according to claim 1, wherein the Bronsted acid is HF, and the Lewis acid is $BF_3$, and
wherein a molar ratio of $BF_3$ to the reaction starting material is from 0.2 to 2.5.

7. The method according to claim 1, wherein the Bronsted acid is HCl, and the Lewis acid is $AlCl_3$, and
wherein a molar ratio of HCl to the reaction starting material is from 0.0001 to 0.3.

8. The method according to claim 1, wherein the Bronsted acid is HCl, and the Lewis acid is $AlCl_3$, and
wherein a molar ratio of $AlCl_3$ to the reaction starting material is from 0.2 to 2.5.

9. The method according to claim 1, wherein the reaction starting material is contacted with the carbon monoxide to react at a reaction pressure of from 1.0 MPaG to 3.0 MPaG.

10. The method according to claim 1, wherein the reaction starting material is the mixture of the 1,4-dialkylbenzene and the 1,3-dialkylbenzene.

11. The method according to claim 10, wherein the reaction starting material is contacted with the carbon monoxide to react at a temperature in a range of from −30° C. to 30° C.

12. The method according to claim 11, wherein the reaction starting material is contacted with the carbon monoxide to react at a reaction pressure of from 1.0 MPaG to 3.0 MPaG.

13. The method according to claim 12, wherein the Bronsted acid is HF, and the Lewis acid is $BF_3$, and
wherein a molar ratio of HF to the reaction starting material is from 5.0 to 25.0.

14. The method according to claim 12, wherein the Bronsted acid is HCl, and the Lewis acid is $AlCl_3$, and
wherein a molar ratio of HCl to the reaction starting material is from 0.0001 to 0.3.

15. The method according to claim 1, wherein the reaction starting material is the 1,4-dialkylbenzene.

16. The method according to claim 15, wherein the reaction starting material is contacted with the carbon monoxide to react at a temperature in a range of from −30° C. to 30° C.

17. The method according to claim 16, wherein the reaction starting material is contacted with the carbon monoxide to react at a reaction pressure of from 1.0 MPaG to 3.0 MPaG.

18. The method according to claim 17, wherein the Bronsted acid is HF, and the Lewis acid is $BF_3$, and
wherein a molar ratio of HF to the reaction starting material is from 5.0 to 25.0.

19. The method according to claim 17, wherein the Bronsted acid is HCl, and the Lewis acid is $AlCl_3$, and
wherein a molar ratio of HCl to the reaction starting material is from 0.0001 to 0.3.

20. The method according to claim 17, wherein the Bronsted acid is HCl, and the Lewis acid is $AlCl_3$, and
wherein a molar ratio of $AlCl_3$ to the reaction starting material is from 0.2 to 2.5.

* * * * *